United States Patent [19]

Williamson et al.

[11] Patent Number: 5,146,922
[45] Date of Patent: Sep. 15, 1992

[54] VOLUMETRIC MEASUREMENT OF A BODY CAVITY OF A PATIENT

[75] Inventors: Ian G. Williamson, Southampton; David H. Kerridge, Wiltshire, both of England

[73] Assignee: National Research Development Corporation, London, England

[21] Appl. No.: 678,943

[22] PCT Filed: Oct. 17, 1990

[86] PCT No.: PCT/GB90/01604
§ 371 Date: Apr. 15, 1991
§ 102(e) Date: Apr. 15, 1991

[87] PCT Pub. No.: WO91/05510
PCT Pub. Date: May 2, 1991

[30] Foreign Application Priority Data

Oct. 17, 1989 [GB] United Kingdom ............ 8923343

[51] Int. Cl.$^5$ ............................................. A61B 5/103
[52] U.S. Cl. ........................................ 128/774; 73/149
[58] Field of Search ............ 128/748, 774; 606/196, 606/199; 73/149

[56] References Cited

U.S. PATENT DOCUMENTS

| | | | |
|---|---|---|---|
| 3,453,881 | 7/1969 | Keng | 73/149 |
| 3,769,834 | 11/1973 | Fletcher et al. | 128/774 |
| 4,369,652 | 1/1983 | Gundlach | 73/149 |

FOREIGN PATENT DOCUMENTS

| | | |
|---|---|---|
| 0215433 | 3/1987 | European Pat. Off. . |
| 3120135A1 | 9/1982 | Fed. Rep. of Germany . |
| 8519715 | 12/1985 | Fed. Rep. of Germany . |
| 9259 | 4/1910 | United Kingdom . |
| 341306 | 1/1931 | United Kingdom . |
| 414947 | 8/1934 | United Kingdom . |
| 1220313 | 1/1971 | United Kingdom . |
| 1447270 | 8/1976 | United Kingdom . |
| 2060911A | 5/1981 | United Kingdom . |

*Primary Examiner*—Max Hindenburg
*Attorney, Agent, or Firm*—Nixon & Vanderhye

[57] ABSTRACT

A method of volumetric measurement of a first closed space of unknown volume which comprises communicating the first space with a second closed space of known volume, changing the known volume of the second space by a predetermined amount, obtaining representations of the pressures in the spaces respectively with the second space at its original known volume and its changed volume, and determining a measure of the unknown volume of the first space from the known volume, the volume change and pressure representations. The method is preferably applied to medical usage for diagnostic purposes with the first space being a body cavity, such as the nasal airway for which a small volume correlates with predisposition to glue ear.

16 Claims, 1 Drawing Sheet

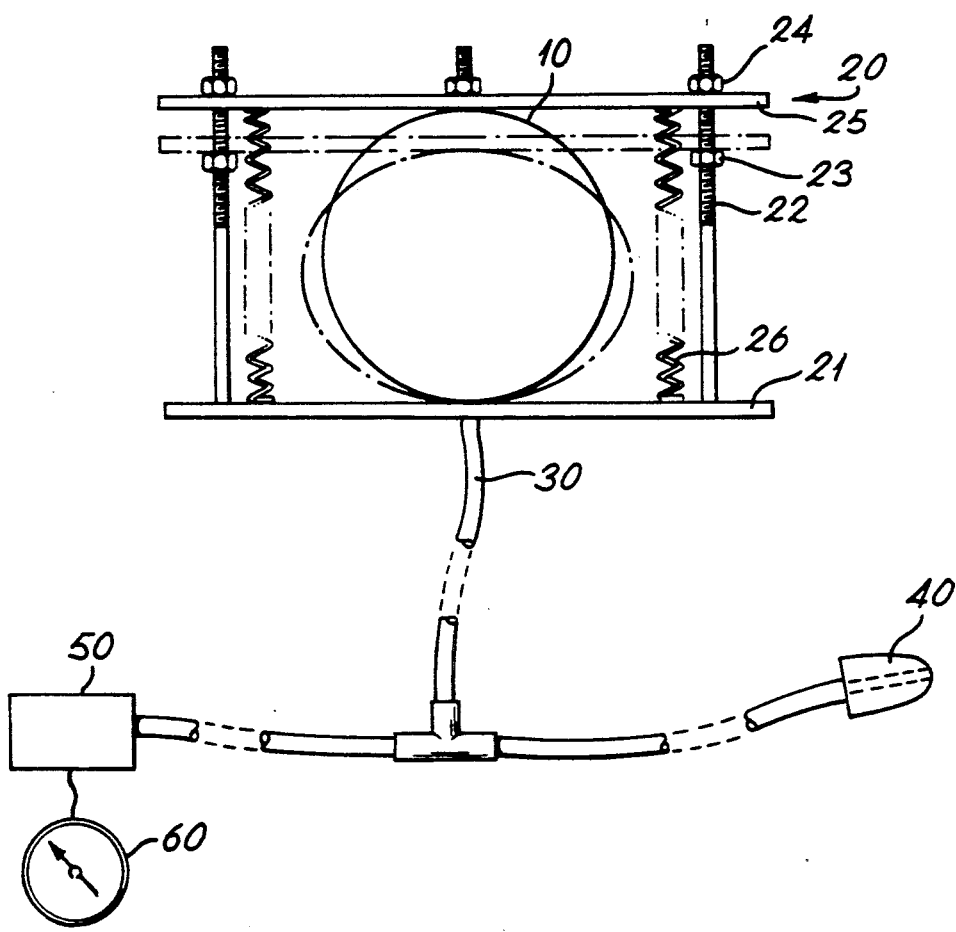

VOLUMETRIC MEASUREMENT OF A BODY CAVITY OF A PATIENT

This invention has been achieved and developed to date primarily in connection with the measurement of nasal volume and it is accordingly both appropriate and convenient to describe the invention in relation to such application. However, it is to be understood that the invention is open to other applications of medical and non-medical form.

The primary interest arises from the proposition that a predisposition to the condition known as 'glue ear' correlates with a less than normal nasal airway size. This condition is a common cause for surgical treatment in children for whom delayed development is otherwise a consequence. In fact such impaired development has often already occurred before treatment insofar as treatment is typically only prescribed when the condition is clearly recognised from recurrence.

Given this situation, a satisfactory means and/or procedure for providing a measure of nasal airway size is of potential benefit because it can give an early indication for treatment.

A proposal for such a procedure has in fact recently been made by A. J. Parker and A. R. Maw as described in a paper entitled "Treatment of glue ear in relation to radiographic palatal airway size a predictor for outcome following adenoidectomy?" published in The Journal of Laryngology and Otology, January 1989, Vol. 103, pp 66-70. However, while this proposal may be of benefit for the purpose at hand, it is questionable whether the necessary cephalometric radiography of children can be viewed as a desirable procedure from other points of view.

An object of the present invention is to improve this situation whereby nasal airway size can be indicated in a more benign and therefore acceptable manner by way of nasal volume.

To this end the invention involves, in more general procedural terms, the volumetric measurement of a first closed space of unknown volume by communicating the same with a second closed space of known volume, changing the volume of the second space by a predetermined amount, obtaining representations of the pressures in the spaces respectively with the second space at its original known volume and its changed volume, and determining a measure of the unknown volume of the first space from the known volume, the volume change and the pressure representations.

In another aspect the invention provides apparatus for carrying out such a procedure.

The volumetric determination of the invention rests on an application of Boyles law, according to which $PV/T$ is constant for a gas, where P, V and T respectively denote pressure, volume and temperature. For the purposes of the invention it is assumed that the temperature, or temperatures, in the two spaces will remain unchanged to the extent that an acceptable measure is obtained. Also a similar assumption is made in respect of the unknown volume which is not necessarily, as in the case of the nasal airway for example, defined by a rigid boundary. These assumptions have in fact been found to be reasonable if the volumetric change represents a small proportion of the initial combined volume of the two spaces and if the volume change and related pressure measurement are effected within a short period of time.

In the case of the nasal airway the space of interest is, of course, not normally closed: it is open to the atmosphere by way of the two nostrils and to the mouth and lungs by way of the palate. In application of the invention to measurement of nasal airway volume it is accordingly proposed that a suitable nasal plug carrying a tube for communication with the second space be sealingly located in one nostril, while the other nostril is held closed manually or by a clip when appropriate. Alternatively, the second space can be communicated with both nostrils by way of a nasal mask sealingly located around the nose. In either case, the palate can at the same time be closed by having the patient effect a forced oral expiration, such as by blowing through a straw or other tube. Also, in such application of the invention, the volumetric change in the second space is preferably an increase whereby a related pressure reduction occurs, this being less likely to cause leakage through the palate than a pressure rise, although such leakage is in any event most unlikely for a modest level of pressure change caused by a proportionately small volume change.

In order to further clarify the invention, the same is described below by way of example with reference to the accompanying drawing which diagrammatically illustrates an embodiment of apparatus according to the invention, which embodiment has been employed in development of the invention to date for application to nasal airway volume measurement.

In the drawing the second space of the invention is defined by the space within a hollow resilient spherical ball 10. This ball is held in a structure 20 whereby the volume of its space can be changed between two values corresponding respectively with a distorted configuration and a less distorted or undistorted rest configuration for the ball.

The structure 20 comprises a base 21 on which the ball is supported. Three like rods 22 project from the base in parallel manner uniformly spaced around the ball. Each rod is threaded and has engaged on it two nuts 23, 24 at first and second predetermined spacings from the base so that the sets of nuts 23, 24 on the rods form like parallel arrays. The nuts 23 nearer to the base are at a first spacing which is less than the distance the ball extends from the base. A plate 25 extends between these arrays, the plate being apertured for clearance engagement around the rods in assembly of the structure 20. Three compression springs 26 are located uniformly around the ball to act between the base and plate whereby the plate is normally engaged against the nuts 24 most distant from the base.

The interior of the ball is communicated by way of flexible tubing 30 with a bored nasal plug 40 and also with a pressure transducer 50, the transducer providing an output which can be recorded and displayed as denoted by a meter 60.

Use of this apparatus is generally as indicated in the introductory discussion above. As a preliminary the plate 25 is urged against the springs 26 to engage the nuts 23 nearer to the base 21 and so distort the ball 10 and reduce the volume of its internal space. In this situation the pressure transducer 50 is calibrated to indicate a set value, suitably zero, at its meter 60 to represent atmospheric pressure. Then the plug 40 is sealingly engaged in one nostril of the patient and the patient executes a forced oral expiration, while the other nostril is held closed and the plate is released to move under spring action into engagement with the nuts 24. This last movement allows the ball to relax to a less distorted configuration with a consequent increase in its internal volume. There will, at the same time, be a related reduction of pressure in the overall closed space formed by the ball, the tubing and the nasal airway, and this reduction will be indicated by way of the pressure transducer and meter. Since measures of the internal volume of the ball in both of its configurations, the internal volume of the tubing if significant, the atmospheric pressure and the pressure reduction are all available by premeasurement or by measurement as a result of the operating procedure, the nasal airway volume can be calculated on the basis that the product of pressure and volume remains constant.

Initial trials with an apparatus and procedure such as just described indicates that children with glue ear do indeed have smaller nasopharyngeal airway volume than those without the disease and that measurement of such a volume accordingly forms a useful basis for diagnosis. By the same token it is indicated that such a volume can be represented for this purpose by the airway space extending from the nares to the point of velopharyngeal closure, with likely inclusion of the paranasal sinuses, as measured by the apparatus and procedure in question.

Regarding the proposals mentioned earlier in relation to the assumptions concerning temperature and a non-rigidly defined unknown volume, it is to be noted that the initial trials involved a volumetric change of 5-10% of the nasal volume in question and an overall time of not more than 5 seconds for effecting the procedure.

Other findings arising during and from the trials include the fact that the nasal plug could, on occasion, be subject to blockage and/or leakage. This situation was improved by use of a plug in the form of a balloon catheter modified by cutting off the distal end of the catheter tube flush with the balloon. However, an alternative to be considered is a nasal mask sealing around the nose, which may avoid possible leakage and also patient discomfort from closure of one nostril while locating a plug in the other.

Another finding was that the volume change might be better effected by a powered compressor or pump 72 to afford greater consistency, with rapidity, of the change, with this change being readily adjustable. In fact it is proposed that the patient blow into tubing 70 having a pressure or other transducer 71 to indicate when sufficient expiratory effort is exerted for the purposes of the procedure and such an indication could usefully trigger a powered volume change.

A related finding is that the provision of a suitable performance by a child for the purpose of the procedure is encouraged by the provision of a sensual stimulus, such as of visual form by way of a 'party blower' facility.

A further finding is that the pressure within the volumes is preferably indicated in progressive and graphic manner as it changes with time during the procedure. This can serve to show, by way of its gradient, whether any significant leakage occurs.

While the invention has been described with more particular reference to the illustrated embodiment and the measurement of nasal airway volume, this is not intended to be limiting. This will already be evident in relation to the embodiment by virtue of the findings just mentioned. As to applications other than to nasal airway measurement: these can be of a medical and non-medical form as noted earlier above. Application can, for example, be made in a similar way to that for nasal airway volume, but with the mouth closed, or with both nostrils closed and communication by way of a mouthpiece, to obtain a measure of residual or other lung volumes. This measure can be of diagnostic value, such as in distinguishing between sinusitis with a blocked ostium and rhinitis. Non-medical application is clearly of potential use in situations where conventional measurement techniques is inappropriate for one reason or another.

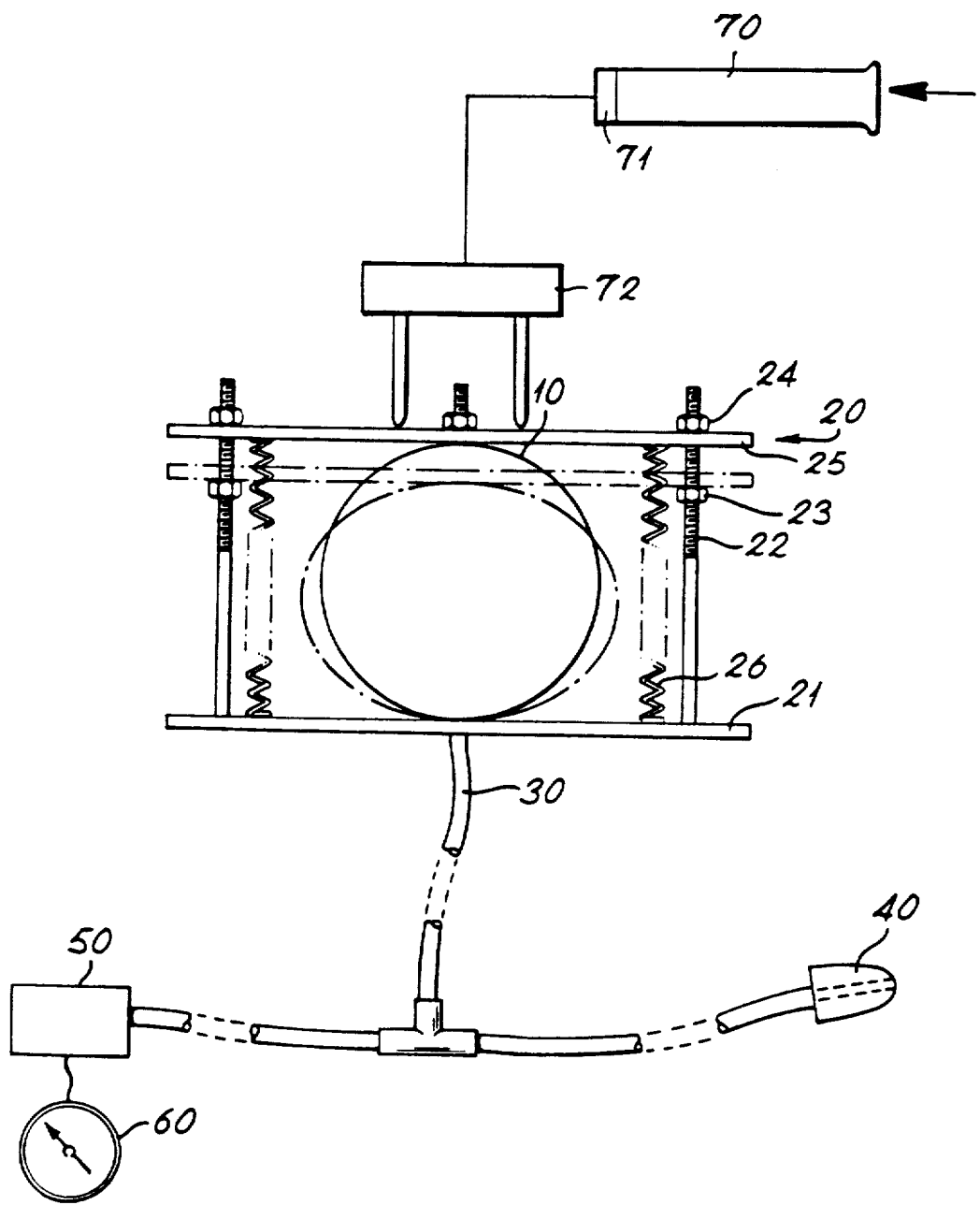

We claim:

1. A method of volumetic measurement of a first closed space of unknown volume, said method comprising the steps of:
    communicating said first closed space with a second closed space of known volume;
    changing said known volume of said second closed space by a predetermined amount;
    obtaining representations of pressures in said closed spaces respectively with said second closed space at its original known volume and its changed volume; and
    determining a measure of said unknown volume of said first closed space from said known volume of said second closed space, the volume change of said second closed space and said pressure representations, said first closed space being a body cavity of a patient, said predetermined amount of known volume change being small relative to the sum of the original known and unknown volumes, said known volume change and related pressure measurement being made within a short period of time.

2. A method according to claim 1, wherein said cavity is the nasal airway and, while the volume change and related measurements are made, such cavity is closed at the palate and communicated by way of at least one nostril.

3. A method according to claim 2, wherein said cavity is communicated by way of one nostril while the other nostril is closed.

4. A method according to claim 2, wherein said cavity is communicated by way of both nostrils.

5. A method according to claim 1, wherein the palate is closed by forced oral expiration on the part of the patient.

6. A method according to claim 1, wherein said known volume change is an increase of the original volume.

7. Apparatus for carrying out volumetric measurement of a body cavity of a patient, comprising:
    a hollow chamber of known volume, said chamber being of variable configuration to change the volume of its space between two known volume values;
    actuating means operably connected to said chamber for changing said volume between said two known volume values;
    means for communicating said chamber with said body cavity in a substantially sealing manner; and
    means for obtaining respective representations of pressure in said chamber at least at each of the said two known volume values.

8. Apparatus according to claim 7, wherein said chamber is resiliently biased towards a configuration having one of said two volume values, and said actuating means being operable releasably to hold said chamber against its bias in a configuration having the other of said two volume values.

9. Apparatus according to claim 7, wherein said actuating means is power-operated to effect said volume change in said chamber.

10. Apparatus according to claim 7, and further comprising a tubular member for use to effect a forced oral expiration by a patient.

11. Apparatus according to claim 10, wherein said member is provided with sensual stimulus means for said patient, said means being operable in response to air movement through said member.

12. Apparatus according to claim 10, wherein said member is provided with transducer means operable in response to air movement through said member to indicate a predetermined level of expiration on the part of said patient.

13. Apparatus according to claim 12, wherein said transducer means acts, when operated, to energize said actuating means.

14. Apparatus according to claim 7, wherein said communicating means comprise a tube connected at one end with said chamber, and at the other end with a bored nasal plug.

15. Apparatus according to claim 7, wherein said communicating means comprise a tube connected at one end with said chamber, and at the other end with a nasal mask.

16. Apparatus according to claim 7, wherein said pressure representation means provides a progressive graphic indication of pressure changes associated with said volume change.

* * * * *

UNITED STATES PATENT AND TRADEMARK OFFICE
CERTIFICATE OF CORRECTION

PATENT NO. : 5,146,922

DATED : September 15, 1992

INVENTOR(S) : Williamson et al

It is certified that error appears in the above-indentified patent and that said Letters Patent is hereby corrected as shown below:

In the Drawing, delete the Drawing Sheet, and substitute therefor the Drawing Sheet, as shown on the attached page.

Signed and Sealed this

Nineteenth Day of October, 1993

Attest:

BRUCE LEHMAN

*Attesting Officer*   *Commissioner of Patents and Trademarks*